US009820667B2

(12) United States Patent
Ting et al.

(10) Patent No.: US 9,820,667 B2
(45) Date of Patent: Nov. 21, 2017

(54) METHOD AND SYSTEM FOR DETECTING HEARTBEAT IRREGULARITIES

(71) Applicant: HEALTHSTATS INTERNATIONAL PTE LTD, Singapore (SG)

(72) Inventors: Choon Meng Ting, Singapore (SG); Wei Nee Serene Chang, Singapore (SG)

(73) Assignee: HEALTHSTATS INTERNATIONAL PTE LTD, Singapore (SG)

( * ) Notice: Subject to any disclaimer, the term of this patent is extended or adjusted under 35 U.S.C. 154(b) by 45 days.

(21) Appl. No.: 14/782,587

(22) PCT Filed: Oct. 17, 2013

(86) PCT No.: PCT/SG2013/000446
§ 371 (c)(1),
(2) Date: Oct. 5, 2015

(87) PCT Pub. No.: WO2014/163584
PCT Pub. Date: Oct. 9, 2014

(65) Prior Publication Data
US 2016/0038048 A1 Feb. 11, 2016

(30) Foreign Application Priority Data

Apr. 4, 2013 (SG) .............................. 201302559-8

(51) Int. Cl.
*A61B 5/04* (2006.01)
*A61B 5/046* (2006.01)
(Continued)

(52) U.S. Cl.
CPC .......... *A61B 5/046* (2013.01); *A61B 5/02108* (2013.01); *A61B 5/02405* (2013.01);
(Continued)

(58) Field of Classification Search
CPC ... A61B 5/0456; A61B 5/046; A61B 5/02405; A61B 5/6898
See application file for complete search history.

(56) References Cited

U.S. PATENT DOCUMENTS 4,163,451 A  8/1979 Lesnick et al.
4,356,827 A 11/1982 Uemura et al.
(Continued)

FOREIGN PATENT DOCUMENTS

CN       1646057 A      7/2005
WO    WO 02030277      4/2002
WO    WO 03/082102   10/2003

OTHER PUBLICATIONS

International Search Report, mailing date Mar. 31, 2014 for corresponding International Application No. PCT/SG2013/000446.
(Continued)

Primary Examiner — Eric D. Bertram
(74) Attorney, Agent, or Firm — Intellectual Property Law Group LLP

(57) ABSTRACT

There is a method and system for detecting heartbeat irregularities comprising the steps of receiving a dataset representative of at least one waveform, the at least one waveform indicative of a subject's heart activity over a predetermined period of time; identifying from the data representative of at least one waveform, a plurality of peaks, each peak corresponding to a heartbeat; identifying from the predetermined period of time the time occurrence of each peak; calculating the difference (duration) between the time occurrence of each peak with its adjacent peak; determining the difference between each duration; classifying the absolute value of the difference into one of at least three intermediate categories; wherein each intermediate category comprises a specified range such that the absolute value is categorized into the intermediate category if it falls between the range; the
(Continued)

intermediate categories further providing an indication of whether the subject has heartbeat irregularity.

13 Claims, 10 Drawing Sheets

(51) Int. Cl.
| | | |
|---|---|---|
| *A61B 5/021* | (2006.01) | |
| *A61B 5/024* | (2006.01) | |
| *A61B 5/0432* | (2006.01) | |
| *A61B 5/0456* | (2006.01) | |
| *A61B 5/0468* | (2006.01) | |
| *A61B 5/00* | (2006.01) | |

(52) U.S. Cl.
CPC ...... *A61B 5/02416* (2013.01); *A61B 5/04012* (2013.01); *A61B 5/0432* (2013.01); *A61B 5/0456* (2013.01); *A61B 5/0468* (2013.01); *A61B 5/6898* (2013.01)

(56) References Cited

U.S. PATENT DOCUMENTS

| | | |
|---|---|---|
| 5,184,615 A | 2/1993 | Nappholz et al. |
| 6,301,499 B1 * | 10/2001 | Carlson .................. A61B 5/222 600/510 |
| 2007/0123787 A1 | 5/2007 | Kitajima et al. |
| 2014/0206944 A1 * | 7/2014 | Jain ..................... A61B 5/02405 600/301 |

OTHER PUBLICATIONS

International Preliminary Report on Patentability completion date Apr. 27, 2015 for corresponding International Application No. PCT/SG2013/000446.

Tsipouras, M.G. et al.: "Arrythmia Classification using the RR—Interval Duration Signal," Computers in Cardiology, 2002 vol. 29, pp. 485-488.

Chazal, P. De et al.: "Automatic Classification of Heartbeats Using ECG Morphology and Heartbeat Interval Features," IEEE Transaction on Biomedical Engineering, Jul. 2004 vol. 51, No. 7 pp. 1196-1206.

Tsipouras, M.G. et al.: "An arrhythmia classification system based on the RR—internal signal," Artificial Intelligence in Medicine, 2005, vol. 33, pp. 237-250.

Jinseok Lee et al., "Atrial Fibrillation Detection using a Smart Phone", Engineering in Medicine and Biology Society (EMBS), 2012 Annual International Conference of IEEE EMBS, Aug. 28-Sep. 1, 2012, pp. 1177-1180.

\* cited by examiner

METHOD AND SYSTEM FOR DETECTING HEARTBEAT IRREGULARITIES

FIELD OF THE INVENTION

The invention relates to a system and method for detecting heartbeat irregularities.

BACKGROUND TO THE INVENTION

The following discussion of the background to the invention is intended to facilitate an understanding of the present invention. However, it should be appreciated that the discussion is not an acknowledgment or admission that any of the material referred to was published, known or part of the common general knowledge in any jurisdiction as at the priority date of the application.

The heart's electrical system controls the rate and rhythm of the heartbeat. With each heartbeat, an electrical signal spreads from the atria of the heart to the ventricles of the same. As the electrical signal travels via the atria, it causes the heart to contract and pump blood into the ventricles. The frequency of electrical signals then reduces to allow the ventricles time to finish filling with blood before signalling the ventricles to contract and pump blood to the lungs and the rest of the body. The ventricles then relax and the heartbeat process restarts all over again.

In a normal heart, the electrical signal is fired off 60 to 100 times a minute—this is the heart rate or pulse. A problem with any part of the heartbeat process can cause an arrhythmia or an irregular heartbeat. The heart may beat too fast, too slowly, too early or too irregularly. For example, in a type of Arrhythmia known as atrial fibrillation, the electrical signals travel through the atria in a fast and disorganized way, causing the atria to quiver instead of contract, leading to an irregularly irregular heartbeat.

Atrial fibrillation (AF) is classified under a category of illness known as cardiac arrhythmia, which is an electrical signal disturbance in the heart causing it to beat erratically. Normally, the heart beats in a steady rhythm often referred to as a sinus rhythm. However, AF interferes the normal regular electrical impulses generated by the sinoatrial node and are overwhelmed by disorganized electrical impulses. This causes the heart to beat inefficiently and contractions of the heart are weaker than normal contractions, resulting in slow flow of blood. AF may occur in episodes lasting from minutes to days ("paroxysmal"), or be permanent in nature.

Due to the irregularity of heartbeat caused by AF, the blood in the heart pools and becomes sluggish or increased turbulence that can result in the blood clotting (thrombus) in the grooves of the heart. Most commonly, atrial fibrillation causes strokes where in the event that a clot leaves the heart and travels to the brain (emboli), blocking the flow of blood through cerebral arteries. A stroke occurs when the blood supply to the brain is blocked and this starves the brain of oxygen and nutrients. This cuts off the blood flow to an area of the brain, damaging the brain cells by starving them of oxygen. This can lead to brain damage occurring and, depending how long the blood supply is cut off, this may be temporary or permanent. Emboli in the brain may result in an ischemic stroke or a transient ischemic attack.

Ischemic Strokes are caused by an interruption of blood flow to the brain because of a blood clot. There are two kinds of ischemic stroke:

Thrombotic—caused by a blood clot in an artery leading directly to the brain

Embolic—caused by a blood clot that travels to the brain from somewhere else in the body.

The conventional method of detecting such conditions has been to use an electrocardiogram (ECG) connected to the patient's chest via electrodes. The ECG records the electrical activity and rhythms of the patient's heart and impulses are recorded as waves and displayed on a screen (or printed on paper). Such ECG devices can be large, cumbersome and non-portable, rendering the patient immobile for the period of measurement, which can be especially difficult in detecting arrhythmia (which occurs irregularly) for prolonged periods of time, in particular if arrhythmia is to be detected over 24 hours or more, or whether arrhythmia is triggered or aggravated by performing certain activities. In addition, ECG may be subjected to errors arising from mechanical-electrical dissociation—i.e. continued electrical rhythmicity of the heart in the absence of effective mechanical function.

A separate problem exists with respect to the methods used for detection of arrhythmia. Present methods are generally device-specific and require complex mathematical manipulations on the signal obtained. There thus exists a need to improve on such methods to reduce the complexity and compatibility with other devices.

It is thus an object of the invention to at least alleviate the above mentioned problems.

SUMMARY OF THE INVENTION

Throughout this document, unless otherwise indicated to the contrary, the terms "comprising", "consisting of", and the like, are to be construed as non-exhaustive, or in other words, as meaning "including, but not limited to".

In the context of the present description of the embodiments of the invention, the term "living body" is a reference to the body at the time of generation of the arterial waveform. The invention is not to be considered as limited to exclude the calculation of a central aortic pressure value from an arterial waveform of a since deceased patient.

In the context of the description of the embodiments of the invention, the term 'pulse waveform' or 'arterial pulse waveform' is understood to be the mechanical manifestation of an electrical heartbeat signal.

The advantages of the invention are as follows:—

A first advantage of the method in accordance with this invention is that it is able to detect arrhythmia by analysing waveforms. This is not restricted to ECG and can be a pulse waveform or more specifically an arterial pulse waveform. A pulse waveform is advantageous as it is free from mechanical-electrical dissociation associated with ECG.

A second advantage of the method in accordance with this invention is that it is able to classify the heartbeats of a person given his arterial pulse waveform, in particular whether the heartbeats are regular, regularly irregular, or irregularly irregular. The simplicity of the method makes it easy to deduce and track the patient's heartbeat type. A third advantage of the method in accordance with this invention is that it can determine between atrial fibrillation from other forms of arrhythmia. This allows for easier identification/classification of the person's heart condition.

In accordance with a first aspect of the invention there is a method for detecting heartbeat irregularities comprising the steps of:—a. receiving a dataset representative of at least one waveform, the at least one waveform indicative of a subject's heart activity over a predetermined period of time; b. identifying from the data representative of at least one waveform, a plurality of peaks, each peak corresponding to a heartbeat; c. identifying from the predetermined period of time the time occurrence of each peak; d. calculating the difference (duration) between the time occurrence of each peak with its adjacent peak; e. determining the difference between each duration calculated in step d; f. classifying the absolute value of the difference into one of at least three intermediate categories; wherein each intermediate category comprises a specified range such that the absolute value is categorized into the intermediate category if it falls between the range; the intermediate categories further providing an indication of whether the subject has heartbeat irregularity.

Preferably, the first intermediate category of the at least three intermediate categories has a specified range of between 0 to 5; the second intermediate category of the at least three intermediate categories has a specified range of between 6 to 11; and the third intermediate category of the at least three intermediate categories has a specified range of 12 and above. More preferably, if all of the classified absolute values occurs in the first intermediate category, with no occurrences in the second and third categories, the at least one waveform is categorized as 'Regular heartbeat'; wherein if there are a number of occurrences |D| in all three Intermediate categories, the at least one waveform is categorized as 'Irregularly irregular' heartbeat; and wherein in all other cases the at least one waveform is categorized as 'Regularly irregular' heartbeat.

Preferably, the waveform indicative of the subject's heart activity over a period of time may be an arterial pulse waveform, an ECG signal or a time series of obtained camera frames captured based on variations in finger skin colour and brightness that occur due to blood pulsation.

Preferably, where the at least one waveform is an arterial pulse waveform, the peaks are determined and identified based on the identification of dicrotic notches as well as the gradient of the upstroke and downstroke identified on the at least one waveform.

Preferably, where the at least one waveform is a time series of obtained camera frames, the method further comprises a conversion step before step c.

Preferably, the conversion step includes the step of accounting for the discrepancy in sampling rates across different mobile devices using the following mathematical expression:—

$$f(HR_n) = (60 \text{ seconds} \times S)/\Delta t_{n-(n+1)}$$

Wherein $f(HR_n)$ denotes beats per minute of each heartbeat, S denotes the sampling rate of the captured waveform; and $t_{n-(n+1)}$ denotes time units in milliseconds between each peak.

In accordance with a second aspect of the invention there is a system for detecting heartbeat irregularities comprising a measurement device for receiving a dataset representative of at least one waveform, the at least one waveform indicative of a subject's heart activity over a predetermined period of time; a processor arranged to receive the dataset and further arranged to:—identify from the at least one waveform, a plurality of peaks, each peak corresponding to a heartbeat; identify from the predetermined period of time the time occurrence of each peak; calculate the difference (duration) between the time occurrence of each peak with its adjacent peak; determine the difference between each duration; and classify the absolute value of the difference into one of at least three intermediate categories; wherein each intermediate category comprises a specified range such that the absolute value is categorized into the intermediate category if it falls between the range; the intermediate categories further providing an indication of whether the subject has heartbeat irregularity.

Preferably, the first intermediate category of the at least three intermediate categories has a specified range of between 0 to 5; the second intermediate category of the at least three intermediate categories has a specified range of between 6 to 11; and the third intermediate category of the at least three intermediate categories has a specified range of 12 and above.

Preferably, if all of the classified absolute values occurs in the first intermediate category, with no occurrences |D| in the second and third categories, the at least one waveform is categorized as 'Regular heartbeat'; wherein if there are a number of occurrences |D| in all three Intermediate categories, the at least one waveform is categorized as 'Irregularly irregular' heartbeat; and wherein in all other cases the at least one waveform is categorized as 'Regularly irregular' heartbeat.

Preferably, the waveform indicative of the subject's heart activity over a period of time may be an arterial pulse waveform, an ECG signal or a time series of obtained camera frames captured based on variations in finger skin colour and brightness that occur due to blood pulsation.

Preferably, where the at least one waveform is an arterial pulse waveform, the peaks are determined and identified based on the identification of dicrotic notches as well as the gradient of the upstroke and downstroke identified on the at least one waveform.

Preferably, where the at least one waveform is a time series of obtained camera frames, the system further comprises a conversion step before the processor identify from the predetermined period of time the time occurrence of each peak.

Preferably, where the conversion step includes the step of accounting for the discrepancy in sampling rates across different mobile devices using the following mathematical expression:—

$$f(HR_n) = (60 \text{ seconds} \times S)/\Delta t_{n-(n+1)}$$

Wherein $f(HR_n)$ denotes beats per minute of each heartbeat, S denotes the sampling rate of the captured waveform; and $t_{n-(n+1)}$ denotes time units in milliseconds between each peak.

Preferably, the measurement device is a real time beat to beat blood pressure monitoring device.

Alternatively, the measurement device is a mobile device with camera and flash capabilities.

In accordance with a third aspect of the invention there is a mobile device having camera and flash capabilities, the mobile device operable to obtain a time series of obtained camera frames captured based on variations in finger skin colour and brightness that occur due to blood pulsation when a subject's finger is positioned against the camera lens and flash; and upon obtaining the time series detects whether the subject has heartbeat irregularity according to the related methods of the first aspect of the invention where a time series of camera frames is obtained.

BRIEF DESCRIPTION OF THE DRAWINGS

The invention will now be described, by way of example only, with reference to the accompanying drawings, in which.

PREFERRED EMBODIMENTS OF THE INVENTION

Particular embodiments of the present invention will now be described with reference to the accompanying drawings. The terminology used herein is for the purpose of describing particular embodiments only and is not intended to limit the scope of the present invention. Additionally, unless defined otherwise, all technical and scientific terms used herein have the same meanings as commonly understood by one or ordinary skill in the art to which this invention belongs.

In accordance with an embodiment of the invention there is a method 110 of detecting heartbeat irregularities and in particular (but not limited to), determining the presence of arrhythmia and differentiating between different types of arrhythmia such as between Atrial Fibrillation (Irregularly irregular heartbeat') and 'regularly irregular heartbeat'. The method 110 comprises steps as illustrated in flow chart form in FIG. 1. FIGS. 2a, 2b and 2c illustrate the different types of heartbeats types, namely 'regular', 'irregularly irregular' and 'regularly irregular' respectively.

Figure 1:
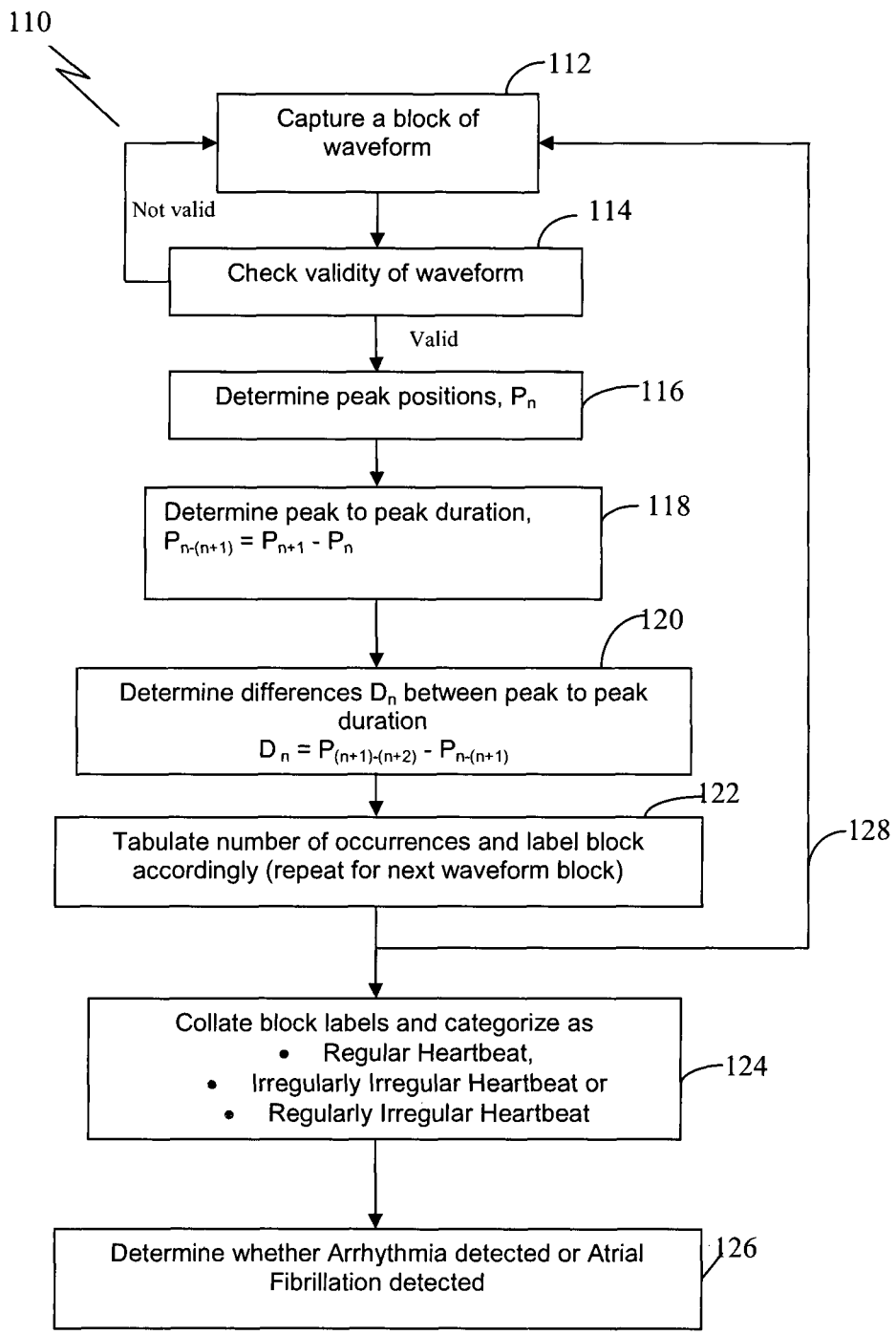
FIG. 1 is a flow chart of a method of determining the presence of arrhythmia in accordance with a first embodiment of the present invention.
Figure 2A:
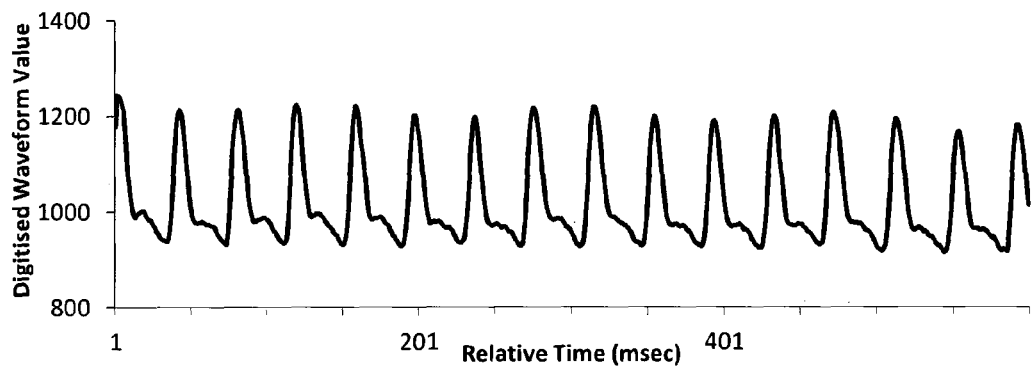
FIGS. 2a, 2b, and 2c are illustrative pulse waveforms showing the various types of heartbeats.
Figure 2B:
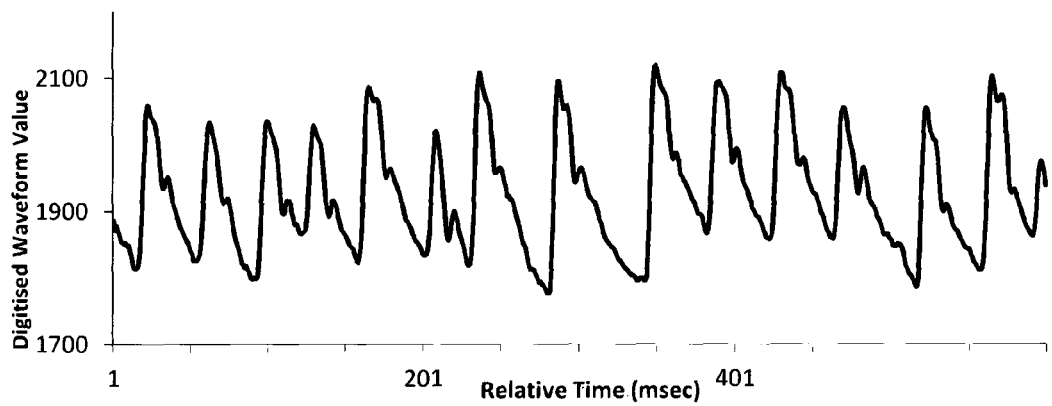
Figure 2C:
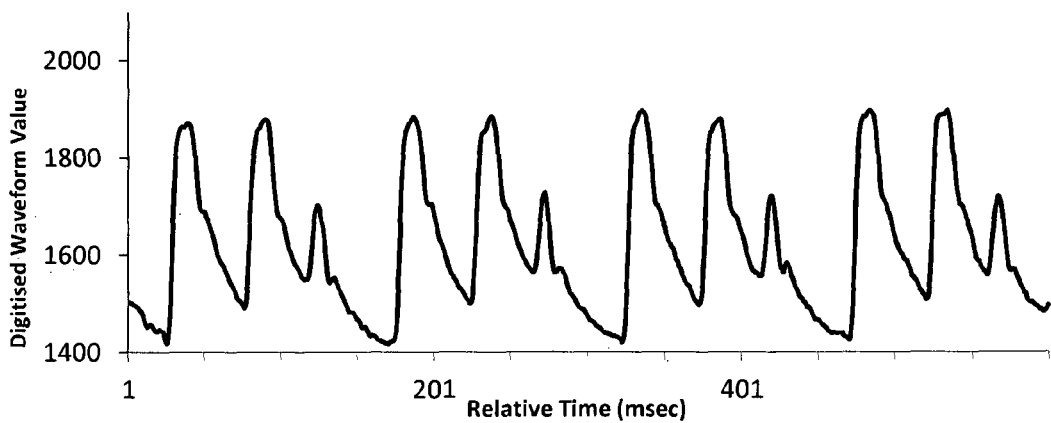

As shown in FIG. 1, the method 110 commences by capturing a block of waveform in step 112. In this embodiment the waveform block is a pulse waveform. More preferably, the waveform block is an arterial pulse waveform which is a mechanical manifestation of one or more electrical heartbeat signal(s). The block of waveform may be captured by a suitable heart rate monitor or real time beat-to-beat blood pressure monitoring device 202 such as the BPro® device of Healthstats International Pte Ltd. Each waveform block should preferably comprise at least enough heartbeats deemed necessary for determining whether the heartbeats are 'regular', 'irregularly irregular' and 'regularly irregular'. As such, the block of waveform should be captured for a period of time as predetermined by a user or medical practitioner. The predetermined period of time may be any period of time between 5 to 60 seconds for example, as long as the period of time is adequate for purpose of analysis and classification. Preferably the block of waveform is between 8 to 30 seconds to capture a block of waveform comprising enough heartbeats for determining regularity or irregularity. Longer or shorter periods of time may be utilized or determined by the user or medical practitioner depending on the measurement device used to capture the block of waveform.

A factor for determining the predetermined period of time is based on the sampling rate of the measurement device 202 used to obtain the block of waveform. For example, a measurement device 202 having sampling rate for obtaining arterial waveform data at 60 Hertz (Hz) require around 5 to 8 seconds to obtain the necessary data to determine a pulse waveform. A measurement device 202 having sampling rate of less than 60 Hz may require longer time to obtain the pulse waveform necessary for analysis.

A measurement device having a sampling rate of 60 Hz at 5 to 8 seconds will obtain about five heart beats, which is deemed suitable for determining whether the heart beats are 'regular', 'irregularly irregular' or 'regularly irregular'.

After the block of waveform is captured, the method 110 may check whether the waveform is valid based on step 114. An exemplary valid waveform should typically have up-slopes 114a and down-slopes 114b signifying the pumping of the ventricular valves. There are existing methods of determining whether a block of waveform is valid and any one of them may be used.

Upon determining that the block of waveform is a valid waveform, the method goes on by determining and identifying the number of peak positions on the obtained pulse waveform within the predetermined block of time in step 116. Each peak position corresponds to a heartbeat. For purpose of naming convention, the peak positions are labelled $P_1, P_2, P_3, \ldots P_n$. A suitable method for determining and identifying the peak positions and heartbeats on the pulse waveform is based on the identification of dicrotic notches as well as the gradient of the upstroke and downstroke as described in WO/2002/030277 and will not be further elaborated.

Once the peak positions are determined and identified, the method goes on in step 118 to determine the peak to peak duration (duration between each heartbeat) using equation (1):

$$P_{n-(n+1)} = P_{n+1} - P_n \quad (1)$$

Wherein $P_{n-(n+1)}$ denotes the total number of sampling points (or relative time units in milli-seconds) between each peak. Typically, a 10 second block is preferably used because under normal conditions a healthy human heart beat should not deviate by more than 5 beats per minute.

Upon determining the peak-to-peak duration, the difference between each peak to peak duration, $D_n$ (typically measured in terms of normalized or relative time scale in milliseconds), can then be calculated in step 120 using equation (2).

$$D_n = P_{(n+1)-(n+2)} - P_{n-(n+1)} \quad (2)$$

Figure 3A:
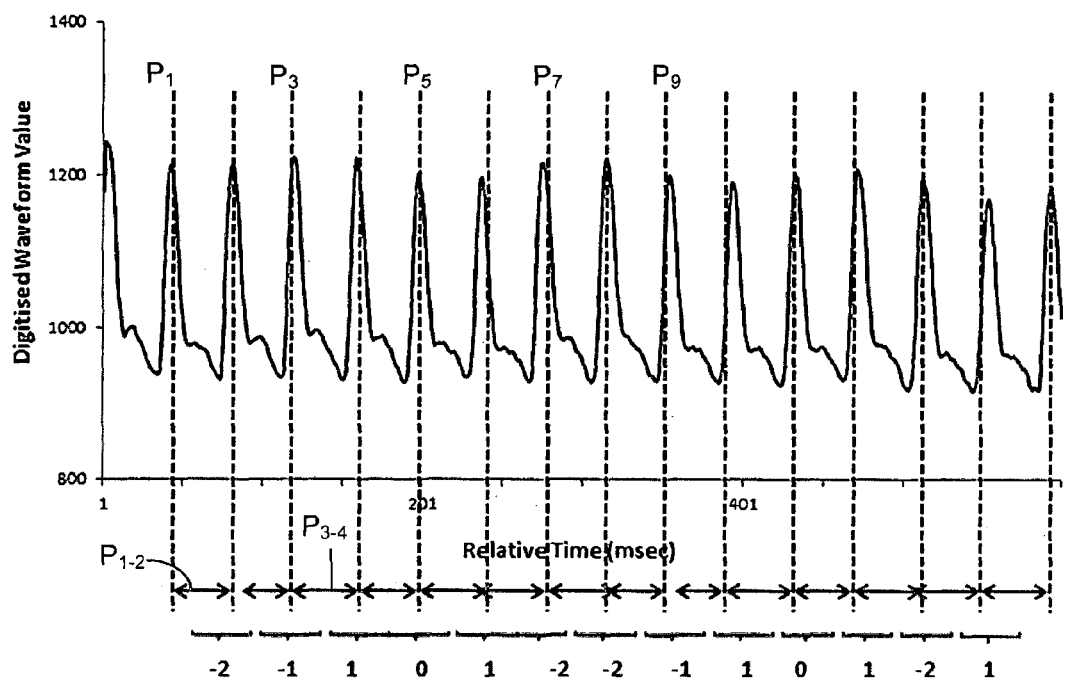
FIGS. 3a, 3b, and 3c are illustrative pulse waveforms with additional segmentation to show how the peaks and peak differences are calculated for the various types of heartbeats.
Figure 3B:
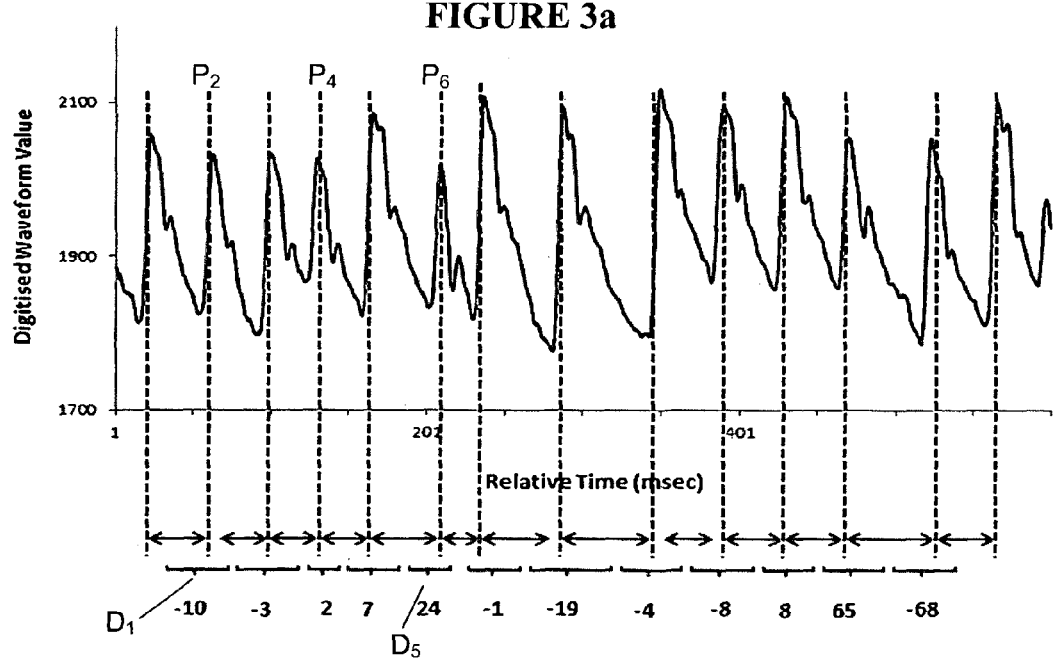

For example in FIG. 3a; $D_1 = P_{2-3} - P_{1-2} = -2$; $D_2 = P_{3-4} - P_{2-3} = -1$;

in FIG. 3b; $D_1 = -10$; $D_5 = 24$; etc.

The obtained $D_n$ will be next categorized into at least three intermediate categories based on its absolute value i.e. $|D_n|$. (step 122). Each intermediate category comprises a range of the absolute value. The three sub-categories (A, B, and C) may be:—

A—where $|D_n|$ is between 0 to 5;
B—where $|D_n|$ is between 6 to 11;
C—where $|D_n|$ is equals or greater than 12.

Using the $D_1 = -10$ and $D_5 = 24$ of FIG. 3b as examples, $D_1$ has an absolute value of 10 and will thus be categorized under category B and $D_5$ has an absolute value of 24 and will thus be categorized under category C.

The method 110 will also collate the number of occurrences in categories A, B and C.

The method 110 then determines whether Arrhythmia or Atrial Fibrillation was detected based on the treatment of the intermediate categories according to the following rules:—

If all the number of occurrences |D| occurs in Intermediate category A only (i.e. with no occurrences in intermediate categories B and C, the pulse waveform block is categorized as 'Regular heartbeat';

If there are a number of occurrences |D| in all Intermediate categories A, B and C, the pulse waveform block is categorized as 'Irregularly irregular' heartbeat;

For all other cases, the pulse waveform block is categorized as 'Regularly irregular heartbeat.

(see step 126)

Optionally, to improve accuracy, steps 112, 114, 116, 118, 120, 122 may be repeated for additional blocks of waveform for the same subject (step 128). Typically steps 112, 114, 116, 118, 120, 122 may be repeated for preferably at least 3 waveform blocks, and optionally recommended at around 5 to 10 waveform blocks.

Figure 3C:
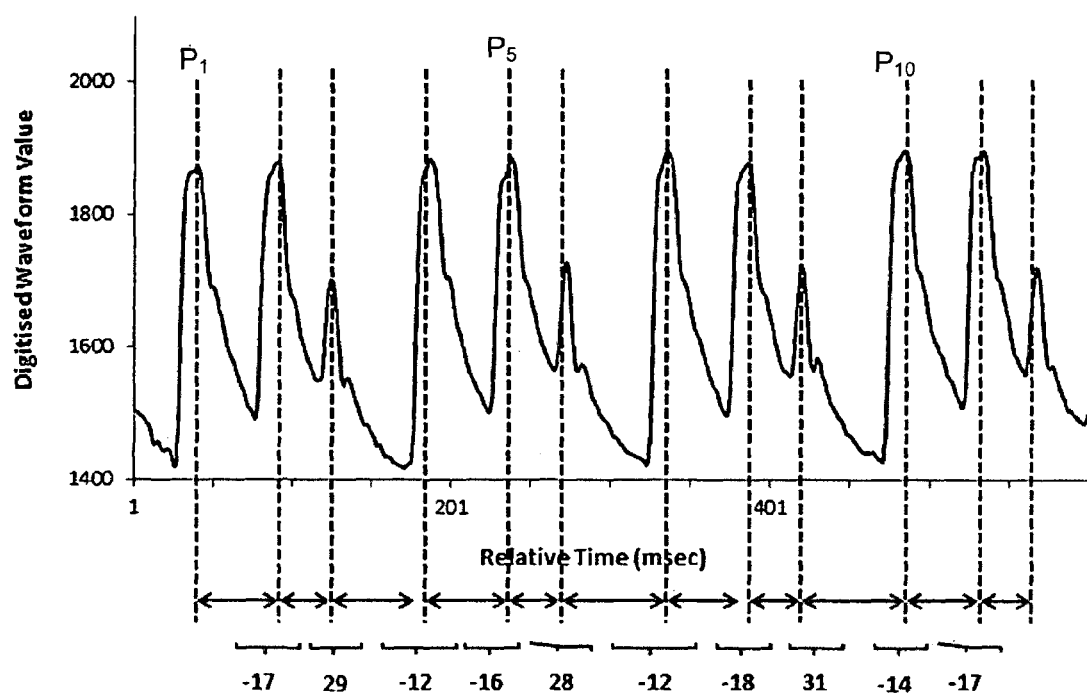

FIGS. 3a, 3b and 3c show how the method determines peak positions 116 and determines the peak to peak duration 118 and displaying the differences between peak to peak 120, $D_n$, below the respective graphs.

Figure 4A:
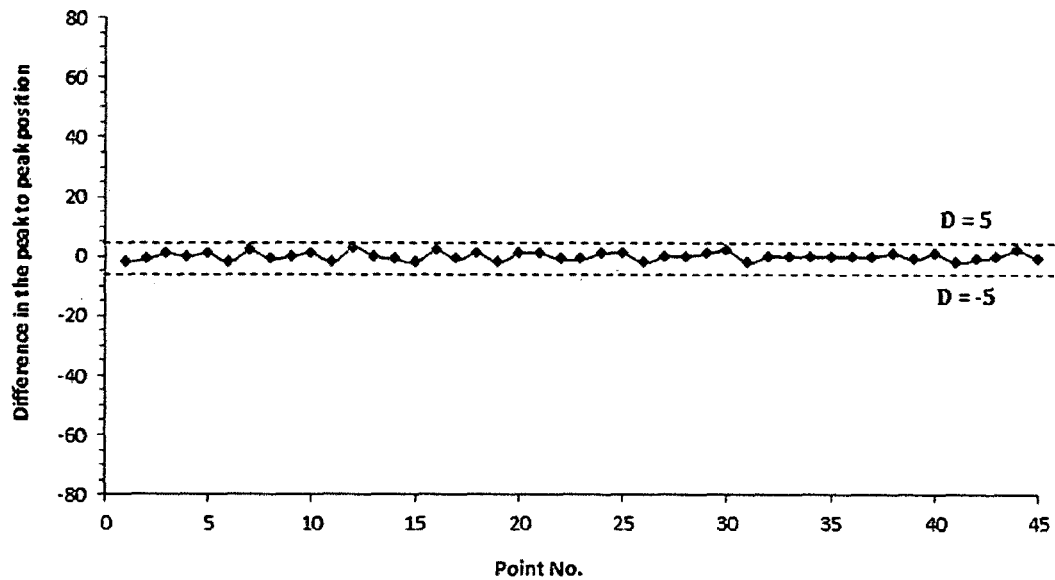
FIGS. 4a, 4b, and 4c are illustrative plots showing the differences in peak to peak duration for the various types of heartbeats.
Figure 4B:
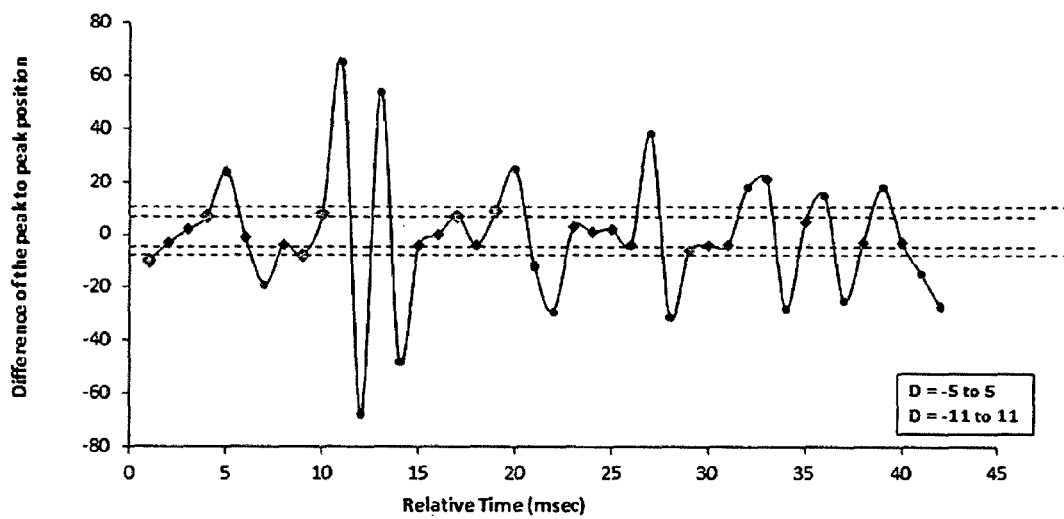
Figure 4C:
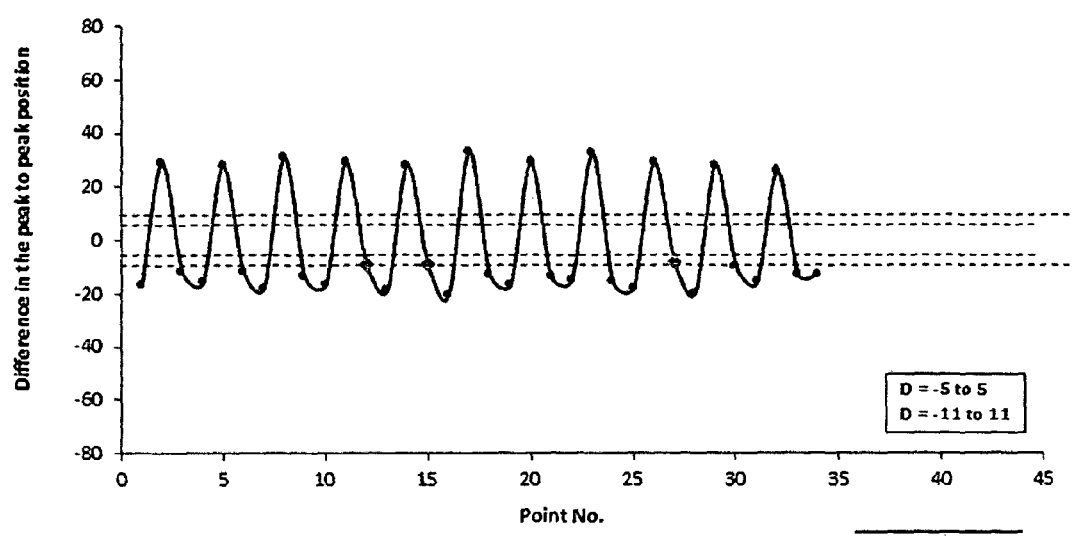
Figure 5:
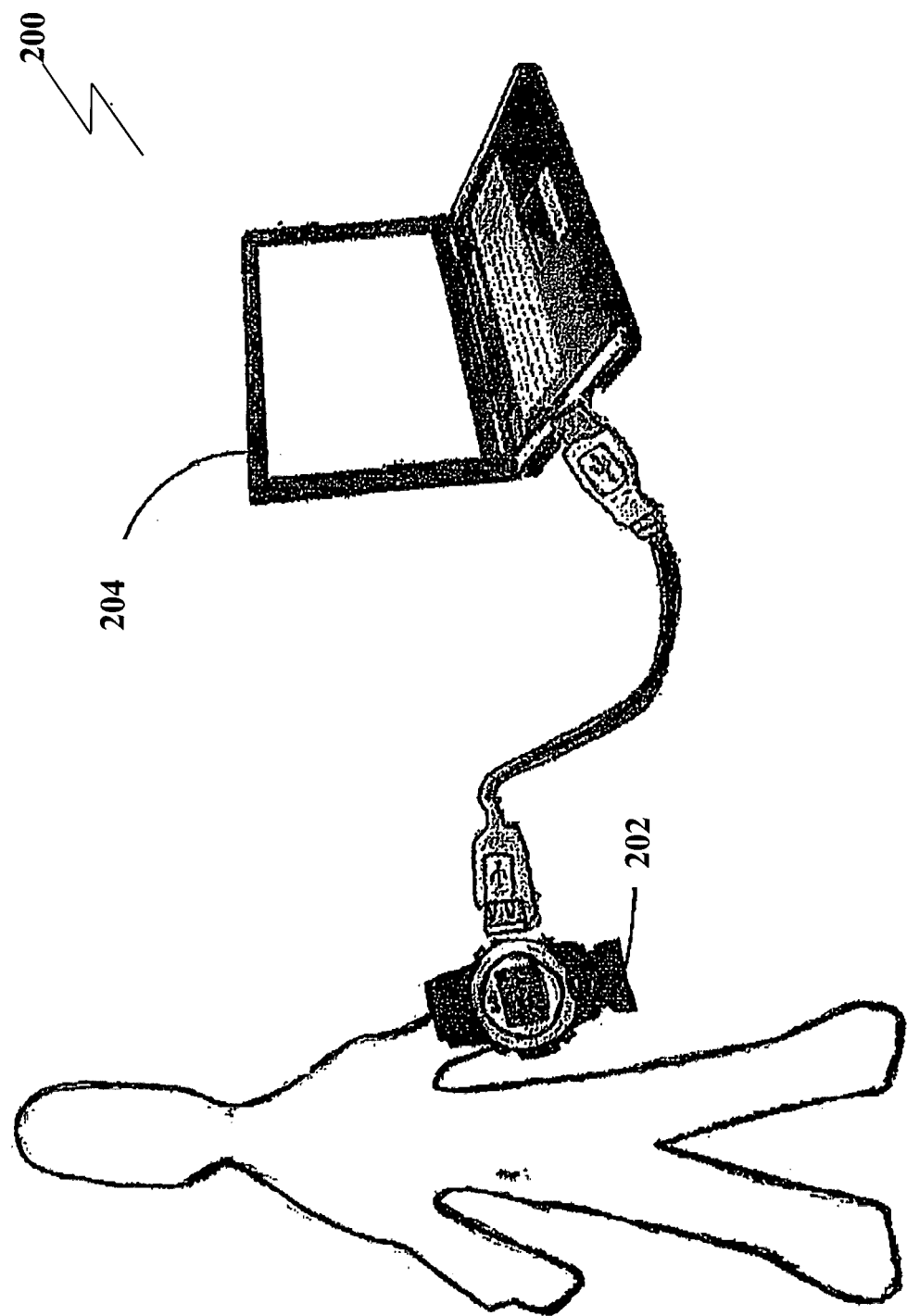
FIG. 5 is a system diagram of the invention in accordance with another embodiment of the invention.
Figure 6A:
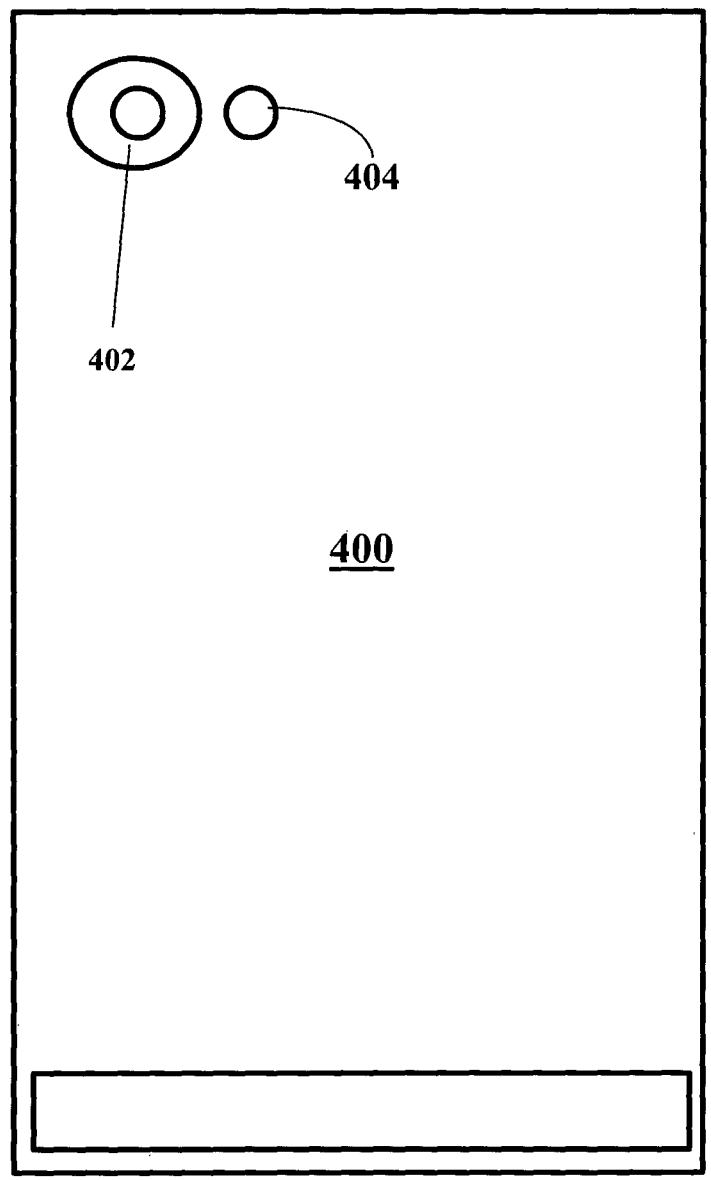
FIGS. 6a to 6c are illustrations of another embodiment of the invention wherein a mobile device is used for the acquisition of data and the detection of arrhythmia; and Other arrangements of the invention are possible and, consequently, the accompanying drawings are not to be understood as superseding the generality of the preceding description of the invention.
Figure 6B:
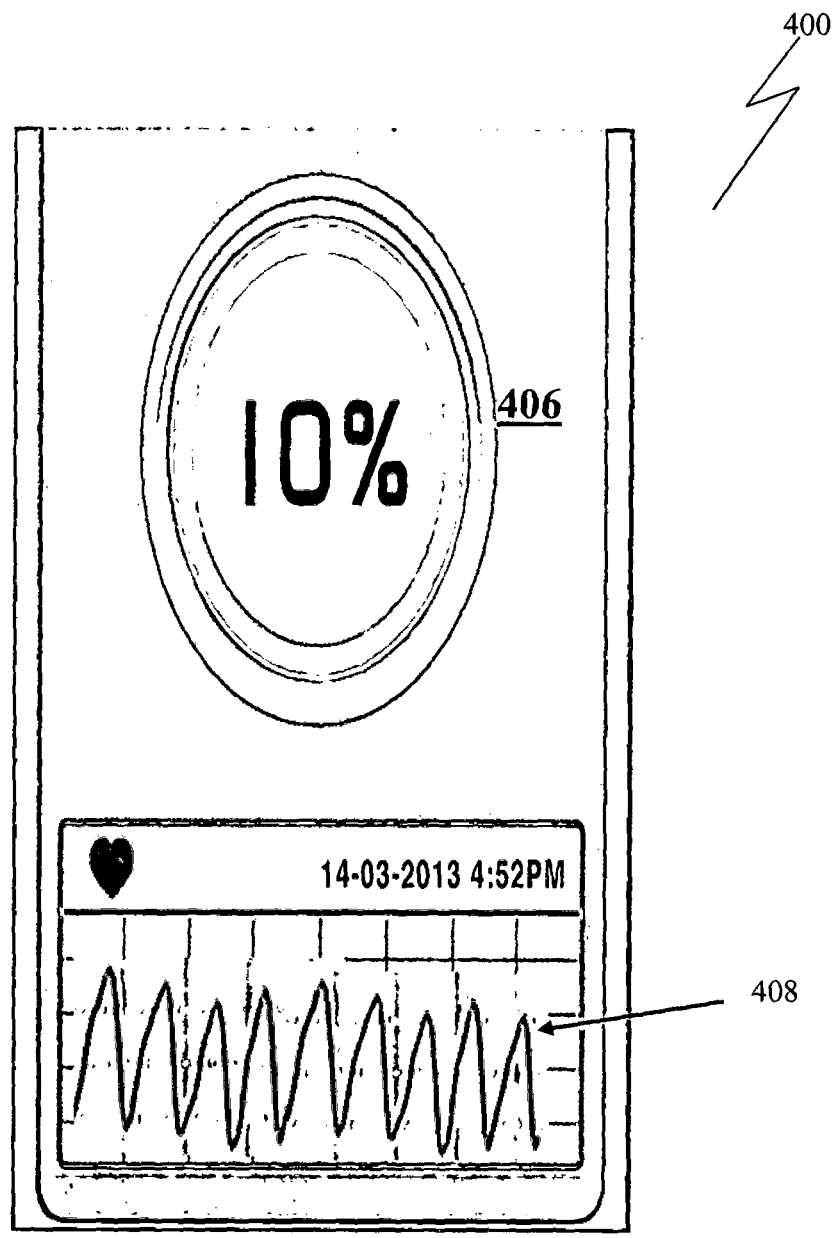
Figure 6C:

It can be seen from plotting out the differences between peak to peak duration 120, $D_n$, for the various heartbeats show different graphs in FIGS. 4a, 4b and 4c for the regular heartbeat, irregularly irregular heartbeat (atrial fibrillation) and regularly irregular heartbeat (arrhythmia) respectively. From the trends of these plots, the method can then determine what type of heartbeat for each block of waveforms and thereafter determine one of three scenarios:

1) No arrhythmia detected—this conclusion, is reached if all the blocks of waveforms are classified as regular heartbeats.
2) Atrial fibrillation detected—this conclusion is reached if any irregularly irregular heartbeats are found in the blocks of waveforms.
3) Arrhythmia detected—this conclusion is reached if there are no irregularly irregular heartbeats found in the blocks of waveforms, and there are instances of regularly irregular' heartbeats found.

In accordance with another embodiment of the invention there is a system 200 of determining the presence of arrhythmia. The system 200 comprises a pulse waveform measurement device 202, preferably arterial pulse waveform measurement device for obtaining pulse waveform from a subject (typically a person). The measurement device may be invasive or non-invasive, as long as the measurement device is capable of obtaining real time beat-to-beat pulse waveform. This is to be distinguished from pulse waveforms obtained based on extrapolation or averaging methods.

The arterial pulse waveform measurement device 202 may preferably be a non-invasive real-time beat-to-beat blood pressure monitoring device such as the BPro® device of Healthstats International Pte Ltd.

System 200 further comprises a processing device 204 for obtaining and storing the arterial pulse waveform measurements obtained. The processing, device may be a computer or mobile device as known to a skilled person in the art. The mobile computing device may optionally be integrated with the non-invasive real-time beat-to-beat blood pressure monitoring device 202 as described above.

Upon receipt of the arterial pulse waveform measurements, the processing device is operable to perform the method 110 to determine if Arrhythmia is present or absent, and if present, whether it is atrial fibrillation.

In accordance with another embodiment of the invention, where like reference numerals designate like features, there is a mobile device 400 for determining the presence of arrhythmia. Mobile device 400 is preferably a smart phone having camera 402 and flash 404 capabilities. Mobile device 400 is capable of installing thereon a dedicated software application 406 (colloquially known as 'apps') suitable for download on an Android™ platform, for example. Dedicated software application 406 is operable to access and activate the camera flash function to detect the heart rate of a person and thereby obtain a waveform. In addition, dedicated software application 406 is capable of implementing the method 110 as described in the earlier embodiment(s) to determine the presence of heartbeat irregularity/arrhythmia.

Instead of a pulse waveform as described in the earlier embodiment(s), the block of waveform as mentioned in step 112 is a time series of obtained camera frames captured based on variations in finger skin colour and brightness that occur due to blood pulsation when a person's finger (preferably but not limited to an index finger of a person) is lightly placed against the camera lens 402 and flash 404.

The detection of variations in finger skin colour and brightness is based on analysing average red component values of the frames or part of the frames taken by the camera. It is to be appreciated that other colour components (blue, green) are generally discarded.

The time series of average red component values of the obtained frames is considered as the captured block of waveform 408 for heart rate measuring. The time series of average red component values of the obtained signal comprises "sharp"—local maxima, each sharp local maxima corresponding to a single heartbeat. It is to be appreciated that the number of heart beats and length of the measurement are the two variables required to calculate the heart rate.

An optional filtering step may be used to filter any noise from the time series if required.

After filtering, the time series signal 408 is converted from the 'obtained frames' form into a form suitable for analysis by the method 110. The time series signal 408 is typically converted into a form where each peak corresponds to a heartbeat.

An example of the conversion comprises three (3) steps, wherein the first and second steps are similar to the concept of step 118 and step 120:—

First step: to determine the time between each peak positions calculated from the first to the $n^{th}$ peak ($t_1 \ldots t_n$); i.e. and Second step: to determine the peak-to-peak duration (i.e. duration between each heartbeat using the following equation (2a)

$$\Delta t_{n-(n+1)} = t_{n+1} - t_n \quad (2a)$$

wherein $t_{n-(n+1)}$ denotes time units in milliseconds between each peak.

It is to be appreciated that the sampling rate of the captured waveform may differ for different waveform(s) captured on different mobile devices 400. For example, thirty (30) frames may be the norm for some mobile devices, while for others it may be higher or lower. To account for the discrepancy in sampling rates across different mobile devices 400, a mathematical equation (3) is used to account for the sampling rate to a form suitable for analysis by method 110.

Third step: Find the number of beats per minute of each heartbeat using the equation (3):

$$f(HR_n) = (60 \text{ seconds} \times S) / \Delta t_{n-(n+1)} \quad (3)$$

Wherein $f(HR_n)$ denotes beats per minute of each heartbeat, and S denotes the sampling rate of the captured waveform.

Once the number of beats per minute of each heartbeat is determined, the method 110 is then used to calculate and tabulate the number of occurrences of 'regular', 'regularly irregular' and 'irregularly irregular' heartbeats in accordance with steps 118, 120, 122, 124 accordingly.

Based on the frame sampling number, a suitable predetermined period of 10-15 seconds for may be chosen.

The current embodiment is advantageous in that it is highly mobile and is targeted at the public, particularly for those who are in the high risk group, such as patients suffering from hypertension, diabetes mellitus, heart disease or have a family history of stroke or sudden death. The App is also useful for patients who know of their AF condition and are being medically treated as it will be able to show the effectiveness of control.

Clinical Trials

To test the efficiency and accuracy of the method 110 in various described embodiments, the algorithm is tested on thirty (30) subjects based on the following parameters:—
time period of measurement—10 seconds;
sampling rate of 60 Hz; and
the non-invasive beat-to-beat blood pressure monitoring device 202—BPrO™.

The clinical results are tabulated in the form of Table 1 below:—

TABLE 1

Clinical Data for Arrhythmia & Atrial Fibrillation (AF) detection algorithm against actual detection

| No. | File Name | Actual detection | Algorithm detected results | Result | Result (True Positive) | Result (True Negative) |
|---|---|---|---|---|---|---|
| 1 | Subject 001 | AF | AF | True positive | 1 | |
| 2 | Subject 002 | AF | AF | True positive | 1 | |
| 3 | Subject 003 | AF | AF | True positive | 1 | |
| 4 | Subject 004 | AF | AF | True positive | 1 | |
| 5 | Subject 005 | AF | AF | True positive | 1 | |
| 6 | Subject 006 | AF | AF | True positive | 1 | |
| 7 | Subject 007 | AF | AF | True positive | 1 | |
| 8 | Subject 008 | AF | AF | True positive | 1 | |
| 9 | Subject 009 | AF | AF | True positive | 1 | |
| 10 | Subject 010 | AF | AF | True positive | 1 | |
| 11 | Subject 011 | AF | AF | True positive | 1 | |
| 12 | Subject 012 | AF | AF | True positive | 1 | |
| 13 | Subject 013 | AF | AF | True positive | 1 | |
| 14 | Subject 014 | Arrhythmia | Arrhythmia | True positive | 1 | |
| 15 | Subject 015 | Arrhythmia | Arrhythmia | True positive | 1 | |
| 16 | Subject 016 | Arrhythmia | Arrhythmia | True positive | 1 | |
| 17 | Subject 017 | Arrhythmia | Arrhythmia | True positive | 1 | |
| 18 | Subject 018 | Arrhythmia | Arrhythmia | True positive | 1 | |
| 19 | Subject 019 | Sinus Rhythm | Sinus Rhythm | True negative | | 1 |
| 20 | Subject 020 | Sinus Rhythm | Sinus Rhythm | True negative | | 1 |
| 21 | Subject 021 | Sinus Rhythm | Sinus Rhythm | True negative | | 1 |
| 22 | Subject 022 | Sinus Rhythm | Sinus Rhythm | True negative | | 1 |
| 23 | Subject 023 | Sinus Rhythm | Sinus Rhythm | True negative | | 1 |
| 24 | Subject 024 | Sinus Rhythm | Sinus Rhythm | True negative | | 1 |
| 25 | Subject 025 | Sinus Rhythm | Sinus Rhythm | True negative | | 1 |
| 26 | Subject 026 | Sinus Rhythm | Sinus Rhythm | True negative | | 1 |
| 27 | Subject 027 | Sinus Rhythm | Sinus Rhythm | True negative | | 1 |
| 28 | Subject 028 | Arrhythmia | Arrhythmia | True positive | 1 | |
| 29 | Subject 029 | Sinus Rhythm | Sinus Rhythm | True negative | | 1 |
| 30 | Subject 030 | Sinus Rhythm | Sinus Rhythm | True negative | | 1 |

Summary of Results:
True Positive (TP): 19
False Negative (FN): 0
True Negative (TN): 11
False Positive (FP): 0
Sensitivity: TP/(TP+FN)=100%
Specificity: TN/(TN+FP)=100%

It is to be appreciated that for the 'actual detection' labelled in the second column, the actual detection may be based on any currently established methods used to determine arrhythmia; sinus rhythm (i.e. normal heartbeat); and Atrial Fibrillation (AF).

It can be appreciated by a person skilled in the art that the above invention is not limited to the embodiments described. In particular, the following modifications and improvements may be made without departing from the scope of the present invention:

As there is a correlation between ECG waveform and arterial pulse waveform, an ECG waveform may be used in place of the pulse waveform (subject to the mechanical-electrical dissociation), so long as the algorithm is able to detect, tabulate and classify the various forms of heartbeats and thereafter make a determination whether arrhythmia not detected, arrhythmia detected or atrial fibrillation detected. Similar methods for converting the obtained ECG waveform to extract salient parameters including:—number of peaks; duration between peaks; etc for usage of the method 110 may be used.

The device can also record and log the date and time whenever arrhythmia or atrial fibrillation is detected.

Instead of obtaining measurements via the camera 402 and flash 404, the integrated mobile device 400 may obtain measurements from the arterial pulse waveform measurement device 202 for analysis. The data from the pulse waveform measurement device 202 may be sent to the mobile device 400 via wireless means such as (but not limited to) infra-red or Bluetooth.

The above is a description of embodiments of a system and method of detecting heartbeat irregularities in accordance with this invention. It is envisioned that those skilled in the art can and will design an alternative embodiment of this invention that infringe on this invention as set forth in the followings claims. It is also to be further appreciated that various aspects of the embodiments as described may be combined to form further embodiments without departing from the scope of the invention.

The invention claimed is:
1. A method for detecting heartbeat irregularities comprising the steps of:
   a. receiving a dataset representative of at least one waveform, the at least one waveform indicative of a subject's heart activity over a predetermined period of time;
   b. identifying from the data representative of at least one waveform, a plurality of peaks, each peak corresponding to a heartbeat;
   c. identifying from the predetermined period of time the time occurrence of each peak;
   d. calculating the duration difference ($P_{n-(n+1)}$) between the time occurrence of each peak with its adjacent peak;
   e. determining the difference ($D_n$) between each duration difference ($P_{n-(n+1)}$) calculated in step d; and
   f. classifying the absolute value ($|D_n|$) of the difference ($D_n$) into one of at least three intermediate categories;
      wherein the first intermediate category of the at least three intermediate categories has a specified range of between 0 to 5; the second intermediate category of the at least three intermediate categories has a specified range of between 6 to 11; and the third intermediate category of the at least three intermediate categories has a specified range of 12 and above; and
      wherein if all of the classified absolute values $|D_n|$ occurs in the first intermediate category, with no occurrences in the second and third categories, the at least one waveform is categorized as 'Regular heartbeat'; wherein if there are a number of occurrences $|D_n|$ in all three Intermediate categories, the at least one waveform is categorized as 'Irregularly irregular' heartbeat; and wherein in all other cases the at least one waveform is categorized as 'Regularly irregular' heartbeat.

2. A method according to claim 1, wherein the waveform indicative of the subject's heart activity over a period of time is an arterial pulse waveform, an ECG signal or a time series of obtained camera frames captured based on variations in finger skin colour and brightness that occur due to blood pulsation.

3. A method according to claim 2, wherein where the at least one waveform is an arterial pulse waveform, the peaks are determined and identified based on the identification of dicrotic notches as well as the gradient of the upstroke and downstroke identified on the at least one waveform.

4. A method according to claim 2, wherein where the at least one waveform is a time series of obtained camera frames, the method further comprises a conversion step before step c.

5. A method according to claim 4, wherein the conversion step includes the step of accounting for the discrepancy in sampling rates across different mobile devices using the following mathematical expression:

$$f(HR_n) = (60 \text{ seconds} \times S)/\Delta t_{n-(n+1)}$$

wherein $f(HR_n)$ denotes beats per minute of each heartbeat, S denotes the sampling rate of the captured waveform; and $t_{n-(n+1)}$ denotes time units in milliseconds between each peak.

6. A mobile device having camera and flash capabilities, the mobile device operable to obtain a time series of obtained camera frames captured based on variations in finger skin colour and brightness that occur due to blood pulsation when a subject's finger is positioned against the camera lens and flash; and upon obtaining the time series detects whether the subject has heartbeat irregularity according to the method of claim 2.

7. A system for detecting heartbeat irregularities comprising
   a measurement device for receiving a dataset representative of at least one waveform, the at least one waveform indicative of a subject's heart activity over a predetermined period of time;
   a processor arranged to receive the dataset and further arranged to:
      identify from the at least one waveform, a plurality of peaks, each peak corresponding to a heartbeat;
      identify from the predetermined period of time the time occurrence of each peak;
      calculate the duration difference ($P_{n-(n+1)}$) between the time occurrence of each peak with its adjacent peak;
      determine the difference ($D_n$) between each duration difference ($P_{n-(n+1)}$); and
      classify the absolute value ($|D_n|$) of the difference ($D_n$) into one of at least three intermediate categories;
   wherein the first intermediate category of the at least three intermediate categories has a specified range of between 0 to 5; the second intermediate category of the at least three intermediate categories has a specified range of between 6 to 11; and the third intermediate category of the at least three intermediate categories has a specified range of 12 and above; and
   wherein if all of the classified absolute values $|D_n|$ occurs in the first intermediate category, with no occurrences in the second and third categories, the at least one waveform is categorized as 'Regular heartbeat'; wherein if there are a number of occurrences $|D_n|$ in all three Intermediate categories, the at least one waveform is categorized as 'Irregularly irregular' heartbeat; and wherein in all other cases the at least one waveform is categorized as 'Regularly irregular' heartbeat.

8. A system according to claim 7, wherein the waveform indicative of the subject's heart activity over a period of time is an arterial pulse waveform, an ECG signal or a time series of obtained camera frames captured based on variations in finger skin colour and brightness that occur due to blood pulsation.

9. A system according to claim 8, wherein where the at least one waveform is an arterial pulse waveform, the peaks are determined and identified based on the identification of dicrotic notches as well as the gradient of the upstroke and downstroke identified on the at least one waveform.

10. A system according to claim 8, wherein where the at least one waveform is a time series of obtained camera frames, the system further comprises a conversion step before the processor identify from the predetermined period of time the time occurrence of each peak.

11. A system according to claim 10, wherein the conversion step includes the step of accounting for the discrepancy in sampling rates across different mobile devices using the following mathematical expression:

$$f(HR_n) = (60 \text{ seconds} \times S)/\Delta t_{n-(n+1)}$$

wherein $f()HR_n)$ denotes beats per minute of each heartbeat, S denotes the sampling rate of the captured waveform; $t_{n-(n+1)}$ denotes time units in milliseconds between each peak.

12. A system according to claim 8, wherein the measurement device is a real time beat to beat blood pressure monitoring device.

13. A system according to claim 8, wherein the measurement device is a mobile device with camera and flash capabilities.

* * * * *